US010251839B2

(12) United States Patent
Lawrence et al.

(10) Patent No.: US 10,251,839 B2
(45) Date of Patent: Apr. 9, 2019

(54) LIPID VESICLES DERIVED FROM OLIVE OIL FATTY ACIDS

(75) Inventors: Nadya Lawrence, Cape May, NJ (US); Rosemarie Lorenzo, Sicklerville, NJ (US)

(73) Assignee: IGI Laboratories, Inc., Buena, NJ (US)

(*) Notice: Subject to any disclaimer, the term of this patent is extended or adjusted under 35 U.S.C. 154(b) by 0 days.

(21) Appl. No.: 12/017,932

(22) Filed: Jan. 22, 2008

(65) Prior Publication Data

US 2009/0186074 A1    Jul. 23, 2009

(51) Int. Cl.
A61K 9/127    (2006.01)

(52) U.S. Cl.
CPC .................................. A61K 9/1272 (2013.01)

(58) Field of Classification Search
CPC ..................................................... A61K 9/127
USPC ...................................................... 424/450
See application file for complete search history.

(56) References Cited

U.S. PATENT DOCUMENTS

| | | | |
|---|---|---|---|
| 4,853,228 A | 8/1989 | Wallach et al. | |
| 4,855,090 A | 8/1989 | Wallach | |
| 4,873,035 A | 10/1989 | Wong | |
| 4,895,452 A | 1/1990 | Yiournas et al. | |
| 4,911,928 A | 3/1990 | Wallach | |
| 4,917,951 A | 4/1990 | Wallach | |
| 4,942,038 A | 7/1990 | Wallach | |
| 5,000,960 A | 3/1991 | Wallach | |
| 5,013,497 A | 5/1991 | Yiournas et al. | |
| 5,019,174 A | 5/1991 | Wallach | |
| 5,019,392 A | 5/1991 | Wallach | |
| 5,023,086 A | 6/1991 | Wallach | |
| 5,104,736 A | 4/1992 | Wallach | |
| 5,147,723 A | 9/1992 | Wallach | |
| 5,160,669 A | 11/1992 | Wallach et al. | |
| 5,213,805 A | 5/1993 | Wallach et al. | |
| 5,219,538 A | 6/1993 | Henderson et al. | |
| 5,229,104 A | 7/1993 | Sottery et al. | |
| 5,234,767 A | 8/1993 | Wallach | |
| 5,256,422 A | 10/1993 | Albert et al. | |
| 5,260,065 A | 11/1993 | Mathur et al. | |
| 5,405,615 A | 4/1995 | Mathur | |
| 5,411,742 A | 5/1995 | Sebag et al. | |
| 5,439,967 A | 8/1995 | Mathur | |
| 5,549,901 A | 8/1996 | Wright | |
| 5,628,936 A | 5/1997 | Wallach | |
| 5,643,600 A | 7/1997 | Mathur | |
| 5,665,380 A | 9/1997 | Wallach et al. | |
| 5,700,679 A | 12/1997 | Wright | |
| 5,756,014 A | 5/1998 | Mathur | |
| 5,908,697 A * | 6/1999 | Roux et al. | 428/402.2 |
| 6,251,425 B1 | 6/2001 | Mathur | |
| 6,387,373 B1 | 5/2002 | Wright et al. | |
| 6,419,963 B1 | 7/2002 | Niazi | |
| 6,458,383 B2 * | 10/2002 | Chen et al. | 424/451 |
| 7,625,967 B2 | 12/2009 | St. Clair | |
| 2004/0053993 A1 * | 3/2004 | Constantinides et al. | 514/458 |
| 2004/0156817 A1 * | 8/2004 | Amari et al. | 424/74 |
| 2006/0024256 A1 | 2/2006 | Wells et al. | |
| 2007/0020342 A1 * | 1/2007 | Modak et al. | 424/642 |
| 2008/0107679 A1 * | 5/2008 | Dilallo et al. | 424/195.17 |

FOREIGN PATENT DOCUMENTS

| | | |
|---|---|---|
| DE | 19634374 A1 | 3/1998 |
| EP | 0267050 A2 | 5/1988 |
| EP | 0301333 A2 | 2/1989 |
| EP | 0317803 A1 | 5/1989 |
| GB | 2135878 | 9/1984 |
| JP | 2001-513779 | 9/2001 |
| JP | 2001-523230 | 11/2001 |
| JP | 2006-290894 | 10/2006 |
| WO | WO-93/03709 A1 | 3/1993 |
| WO | WO-93/08202 A1 | 4/1993 |
| WO | WO-95/13052 A1 | 5/1995 |
| WO | WO-98/50005 A1 | 11/1998 |
| WO | 07/031139 A1 | 3/2007 |

OTHER PUBLICATIONS

Azmin in J. Pharm. Pharmacol. vol. 37, pp. 237-242, 1985.*
Namdeo in Journal of Microencapsulation, vol. 16, # 1, pp. 731-740, 1999.*
Information Disclosure Statement for Application No. PCT/US09/30296, dated Mar. 11, 2009.
B&T Company, Olive in Cosmetics, retrieved online at http://www.btcompany.com/olive_in_cosmetics.asp (2008).
B&T Company, "Products/Olivem®1000," retrieved online at http://www.btcompany.com/olivem1000.asp (2008).
B&T Company, "Products/Olivem®900," retrieved online at http://www.btcompany.com/olivem900.asp (2008).
B&T Company, "Products/Olivem®700," retrieved online at http://www.btcompany.com/olivem700.asp (2008).
Kiwada, Hiroshi et al., "Application of Synthetic Alkyl Glycoside Vesicles as Drug Carriers. I. Preparation and Physical Properties," *Chem. Pharm. Bull.*, vol. 33(2):753-759 (1985).
B&T S.c.I., "Olivem 1000, INCI: Cetearyl Olivate, Sorbitan Olivate," retrieved online at: http://www.lotionerafter.com/reference/Oliven_1000.pdf, 10 pages (2002).
Nippon Yakuji Nippoh Ltd., "Olive Oil," Revised Handbook of Pharmaceutical Excipients, pp. 175-177 (2007).
Japanese Office Action for Application No. 2010-544365, 13 pages, dated Jul. 16, 2013.
Supplementary European Search Report for Application No. 09703999.4, 5 pages, dated Mar. 27, 2013.
Lanigan, Rebecca S. et al., "Final Report on the Safety Assessment of Sorbitan Caprylate, Sorbitan Cocoate, Sorbitan Diisostearate, Sorbitan Dioleate, Sorbitan Isostearate, Sorbitan Olivate, Sorbitan Sesquiisostearate, Sorbitan Sesquistearate, and Sorbitan Triisostearate," International Journal of Toxicology, vol. 21(Suppl. I):93-112 (2002).

(Continued)

*Primary Examiner* — Gollamudi Kishore
(74) *Attorney, Agent, or Firm* — Nelson Mullins Riley & Scarborough LLP; Anthony A. Laurentano; Cynthia L. Kanik

(57) ABSTRACT

Novel lipid vesicle compositions comprising lipids derived from olive oil fatty acids known as olivates, methods of their preparation, and methods of their use in cosmetics, food, dermatologics, and pharmaceuticals.

18 Claims, No Drawings

(56) References Cited

OTHER PUBLICATIONS

Martinez, M.A. Ruiz et al., "Influence of the concentration of a gelling agent and the type of surfactant on the rheological charasteristics of oleogels," II Farmaco, vol. 58:1289-1294 (2003).

Seo, S.-B. et al., "Devleopment of a natural preservative system using the mixture of *Chitosan-Inula helenium* L. extract," International Journal of Cosmetic Science, vol. 24:195-206 (2002).

\* cited by examiner

LIPID VESICLES DERIVED FROM OLIVE OIL FATTY ACIDS

BACKGROUND OF THE INVENTION

Lipid vesicles, also known as liposomes, are substantially spherical structures made of amphiphilic materials having high lipid content, such as phospholipids and surfactants. The lipids of these spherical vesicles are organized in the form of lipid bilayers e.g., multiple onion-like shells of lipid bilayers which encompass an aqueous volume between the bilayers. Paucilamellar lipid vesicles have 2-10 peripheral bilayers surrounding a large, unstructured central cavity which may be filled with water or oil soluble (hydrophobic and hydrophilic) materials.

While lipid vesicles occur naturally in cells where they are involved in intra- and inter-cellular transport, they may also be synthesized for use as model membranes. Other applications include encapsulation and delivery of cosmetic, oral, dermatological, and pharmaceutical ingredients.

SUMMARY OF THE INVENTION

The present invention provides novel lipid vesicle compositions and methods of their preparation. The present invention is based, at least in part, on the development of new lipid vesicles comprising, as the primary structural material, olive oil fatty acid derivatives known as olivates. In particular, the present invention discloses paucilamellar lipid vesicles which have exceptional properties for cosmetic, oral, dermatological, and pharmaceutical uses.

In one aspect, the invention provides lipid vesicle compositions comprising a lipid phase and an aqueous phase, wherein the compositions include at least one lipid bilayer. The components of the lipid phase further include at least one olivate.

In another embodiment, the invention also provides a method of preparing lipid vesicle compositions comprising an olivate. The method includes heating a lipid phase having at least one olivate, separately heating an aqueous phase, mixing the heated lipid phase with the heated aqueous phase to form a solution, and cooling the solution.

DETAILED DESCRIPTION OF THE INVENTION

The present invention provides novel lipid vesicle compositions and methods of their preparation. The present invention is based, at least in part, on the development of new lipid vesicles comprising, as the primary structural material, olive oil fatty acid derivatives known as olivates. In particular, the present invention discloses paucilamellar lipid vesicles which have exceptional properties for cosmetic, oral, dermatological, and pharmaceutical uses.

I. Lipid Vesicle Compositions

In one aspect, the invention provides lipid vesicle compositions comprising a lipid phase and an aqueous phase, wherein the compositions include at least one lipid bilayer comprising an olivate. The olivate may be the primary structural material of the bilayer(s).

Lipid vesicle compositions of the present invention may be unilamellar, multilamellar or paucilamellar. In one embodiment, the vesicles are paucilamellar, e.g., having two or more lipid bilayers surrounding an amorphous central cavity which may be filled with materials. Examples of materials which lipid vesicles of the present invention may encapsulate include, but are not limited to, macromolecules, viruses, immunological adjuvants, hormones, peptides, growth factors, lymphokines, blood proteins, plant hormones and pesticides, radionucleotides, cancer cytostatics, antibiotics, pheromones, porphyrins, fungicides, insect repellants, perfumes and fragrances, oils, fats, and vitamins. For example, the encapsulated material of the vesicles may comprise between about 0% to about 60% of the vesicle by weight.

The term "about" refers to within 10%, preferably within 5%, and more preferably within 1% of a given value or range. The term "about" also includes within an acceptable standard error of the mean, when considered by one of ordinary skill in the art.

In general, the lipid phase makes up approximately 10-70% (by weight) of the lipid vesicles and the aqueous phase makes up the remaining 30-90%.

The present invention features lipid vesicles which are comprised of at least one lipid bilayer. The term "lipid bilayer" refers to the arrangement of amphiphiles having a hydrophilic "head" group attached via ester or ether linkages to a hydrophobic "tail" group. In an aqueous environment, the amphiphiles form a layer of two molecules in which the hydrophobic "tails" are directed to the inside of the bilayer(s) while the hydrophilic "heads" are directed to the outside of the bilayer(s). The hydrophobic tail may be derived from substances such as long chain fatty acids, long chain alcohols and their derivatives, long chain amines, and polyol sphingo- and glycerolipids.

Examples of fatty acids useful in forming the hydrophobic tail of lipid bilayer(s) of the present invention include, but are not limited to, unsaturated fatty acids derived from olive oil, such as oleic acid, linoleic acid, and linolenic acid. Further examples of fatty acids include, but are not limited to, lauric acid, myristic acid, palmitic acid, steric acid, arachidic acid, behenic acid, lignoceric acid, palmitolic acid, ricinoleic acid, caprylic acid, capric acid, and arachidonic acid.

In one embodiment, the lipid bilayers comprise fatty acids and fatty acid esters. Preferably, at least about 5%, at least about 10%, at least 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% (by weight) of the fatty acids and/or the fatty acid esters are derived from olive oil.

In one aspect, the invention pertains to a composition wherein the lipid phase of the lipid vesicles comprise olivates selected from the group consisting of sorbitan olivate, polyethyleneglycol-4 olivate, cetearyl olivate, and mixtures thereof.

The term "olivate" refers to compounds that are formed when olive oil triglycerides (e.g. glycerol trioleate, glycerol trilinoleate, and glycerol trilinolenate) are saponified to form carboxylate salts of olive oil fatty acids. Saponification is base-promoted ester hydrolysis of glycerol triesters, which produces carboxylate salts of the fatty acid and glycerol. For example, potassium olivates may be formed by the reaction of olive oil with potassium hydroxide. Scheme 1 illustrates the saponification of glycerol trioleate, the main component of olive oil, to potassium olivate.

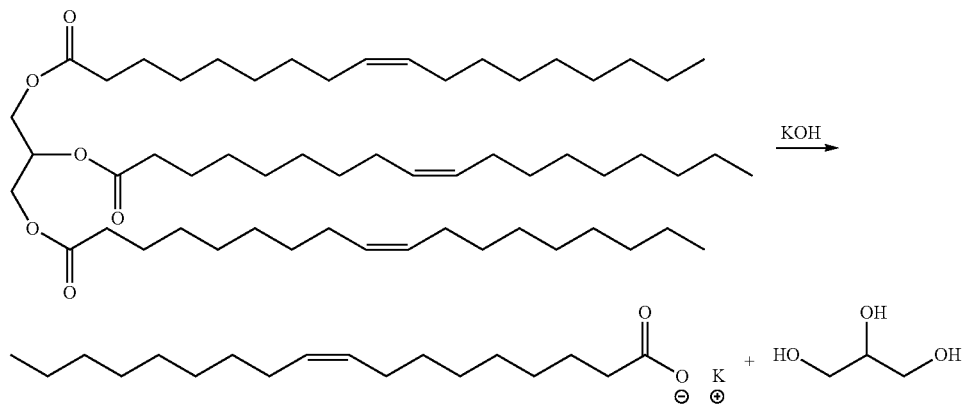

Potassium olivates may react with alcohols such as sorbitan, polyethylenglycol-4 and cetearyl alcohol to form sorbitan olivate, polyethyleneglycol-4 olivate, and cetearyl olivate, respectively.

The lipid bilayers generally comprise between about 0.1% to about 75% of olivate.

The lipid phase of the vesicle compositions of the invention may further comprise sterols. Sterols useful in forming the lipid bilayer(s) include any sterol known in the art to be useful as modulators of lipid membranes. Suitable sterols include, but are not limited to, cholesterol, cholesterol derivatives, cholesterol salts, cholesterol esters, ethoxylated cholesterol, hydrocortisone, phytosterol, avocado unsaponifiables, and mixtures thereof. The amount of sterol may depend up to an extent on whether it competes with any lipophilic material to be encapsulated. In an embodiment, the lipid bilayers generally comprise between about 0% to about 25% of a steroid such as a sterol.

In another aspect of the invention, the vesicles compositions may further comprise an oil, such as a hydrocarbon, caprylic triglyceride, capric triglyceride, mineral oil, soybean oil, squalene oil, sesame oil, olive oil, canola oil, corn oil, rapeseed oil, safflower oil, sunflower oil, palm oil, palm kernel oil, fish oils, flavor oils, paraffin wax, petrolatum, apricot kernel oil, kukui oil, isopropyl stearate, isopropyl palmitate, isodecane, grapeseed oil, golden jojoba, ethylhexyl palmitate, dimethicone, cyclomethicone, dimethicone copolyol, coconut oil, cetearyl ethylhexanoate, castor oil, $C_{12}$-$C_{15}$ alkyl benzoate, borage oil, esters, avocado oil, and water insoluble vitamins. During preparation of the vesicles, the oil partitions to the central core of the vesicles while the remaining lipids are incorporated into the lipid bilayer(s) which surround(s) the core.

In one embodiment, the oil may be a triglyceride such as caprylic triglyceride, capric triglyceride, or mixtures thereof. For example, triglycerides present in the amount of between about 0% to about 60%, between about 5% to about 55%, between about 10% to about 50%, or between about 20% to about 40% of triglyceride by weight.

In another embodiment, the oil may be mineral oil. For example, the lipid vesicle composition may comprise between about 0% to about 50%, between about 10% to about 40% or between about 20% to about 30% mineral oil, by weight.

In a further embodiment, the lipid phase of the lipid vesicles may further comprise a nonionic detergent. The term "nonionic detergent" refers to detergents that do not have ionic groups and thus will not ionize in aqueous solution, such as polyoxyethylene (20) sorbitan monooleate, polyoxyethylene (20) sorbitan trioleate, polyoxyethylene (20) sorbitan monopalmitate, polyoxyethylene (20) sorbitan monostearate, and mixtures thereof. The nonionic detergent may be present in the amount of about 0% to about 2.0%, between about 0.5% to about 1.5%, or about 1.0% by weight.

The compositions of the present invention may also include an aqueous phase comprising water, e.g. deionized water, water soluble or miscible ingredients and, optionally, an antimicrobial agent.

The term "antimicrobial agent" includes to compositions that act as a preservative effective against bacteria, yeast, fungi, and mold. Such agents include, but are not limited to, propylene glycol, diazolidinyl urea, imidazolidinyl urea, methylparaben, propylparaben, phenoxyethanol, caprylyl glycol, and mixtures thereof. For example, the antimicrobial agent may be GERMABEN II (e.g. a mixture of about 56% propylene glycol, about 30% diazolidinyl urea, about 11% methylparaben, and about 3% propylparaben).

The amount of the antimicrobial agent may be selected such that it is effective for its intended purpose. For example, the antimicrobial agent may be present in an amount of about 0% to about 2%, or about 1% by weight.

The vesicles of the present invention may also include targeting molecules, either hydrophilic or amphiphilic, which can be used to direct the vesicles to a particular target in order to allow release of the material encapsulated in the vesicle at a specified biological location. If hydrophilic targeting molecules are used, they can be coupled directly or via a spacer to an OH residue of the lipid. If spacers are used, the targeting molecules can be interdigitated into the hydrophilic core of the bilayer membrane via the acyl chains of these compounds. Preferred hydrophilic targeting molecules include monoclonal antibodies, other immunoglobulins, lectins, and peptide hormones.

In addition to hydrophilic targeting molecules, it is also possible to use amphiphilic targeting molecules. Amphiphilic targeting molecules are normally not chemically coupled to the surfactant molecules but rather interact with the lipophilic or hydrophobic portions of the molecules constituting the bilayer lamellae of the lipid vesicles. Preferred amphiphilic targeting molecules are neutral glycolipids, galactocerebrosides (e.g., for hepatic galactosyl receptors), or charged glycolipids such as gangliosides.

In another aspect, the pH of the lipid vesicle compositions is selected such that the lipid vesicle composition is suitable for its intended use. For example, for use in cosmetics, the pH may be selected such that the composition does not irritate the skin. In a further embodiment, the pH of the lipid composition may be between about 2 to about 8.

II. Methods of Making Lipid Vesicles

Lipid vesicles of the present invention may be formed using the "hot loading" technique disclosed in U.S. Pat. No. 4,911,928, the disclosure of which is incorporated herein by reference. In either case, a lipid phase is formed by blending a primary structural material (e.g. an olivate) and compatible amphiphile(s), with or without sterols or lipophilic materials to be incorporated into the lipid bilayers, to form a homogenous lipid phase. In the "hot loading" technique, a lipophilic phase is made and heated, and is blended with a heated aqueous phase (e.g., water, saline, or any other aqueous solution which will be used to hydrate the lipids) under shear mixing conditions to form the vesicles. "Shear mixing conditions", as used herein, means a shear equivalent to a relative flow of 5-50 m/s through a 1 mm orifice. The paucilamellar lipid vesicles of the disclosure can be made by a variety of devices which provides sufficiently high shear for shear mixing. A device which is particularly useful for making the lipid vesicles of the present invention is described in U.S. Pat. No. 4,985,452, assigned to Micro Vesicular Systems, Inc.

In another aspect, the invention pertains to a method of preparing a lipid vesicle composition. The method includes heating a lipid phase comprising at least one olivate to between about 60° C. to about 80° C. (e.g. about 75° C.); separately heating an aqueous phase to between about 55° C. to about 75° C. (e.g. about 60° C.); mixing the heated lipid phase with the heated aqueous phase to form a solution; and finally cooling the mixed solution to between about 20° C. to about 30° C. (e.g. about 25° C.).

In addition, the method may further comprise adding an antimicrobial agent to the cooled solution, and mixing the solution until homogeneous.

Advantageously, the vesicles of the present invention are stable (e.g., do not separate from the liquid and do not form aggregates) at ambient temperatures (e.g., 20-50° C.). In one embodiment, the vesicles of the invention are stable at temperatures of about 20° C. to about 50° C. for at least 24 hours, one week, one month, two months, three months, or longer. Preferably the vesicles are round, although other shapes may be preferred for particular applications.

In another aspect of the invention, the invention pertains to a lipid vesicle composition for use as an emollient or humectant in an external skin care product for mammals. Preferred mammals include primates, such as humans, chimpanzees, or gorillas; farm animals (e.g. cows, sheep, pigs, horses, goats); lab animals (e.g. rats, mice, monkeys) and pets (e.g. cats, dogs, ferrets). Such a skin care product may include, but is not limited to, day-care, sun-care, baby-care, make-up, or combinations thereof.

The term "emollient" refers to substances which act to prevent water loss to the skin when applied externally. For example, emollients include, but are not limited to cholesterol, squaline and fatty acids, castor oil, almond oil, oleic acid oleyl ester, caprylic triglyceride, capric triglyceride, ocryl dodecanol, cetearyl isonanoate, oleyl alcohol, dioctyl cyclohexane, isopropyl stearate and isopropyl myristate fatty esters.

The term "humectant" includes substance which act to absorb and retain moisture when applied externally. Examples of humectants include, but are not limited to glycerine, propylene glycol, polysaccharides, sorbitol, urea, alphahydroxy acids and sugars.

This invention is further illustrated by the following examples which should not be construed as limiting.

EXAMPLES

Example 1: Preparation of Lipid Vesicle Compositions Using Polyethyleneglycol-4-Olivate, Nonionic Detergent, and Triglyceride The lipid vesicles of this Example were made using polyethyleneglycol-4-olivate. Table 1 lists the materials and proportions used in preparing three different formulations of 50 g preparations of the lipid vesicles of this invention. The following procedure was used to make vesicles of the invention.

The vesicles were formed under shear mixing conditions, as outlined in the procedure above. The components of the lipid phase were weighed out into a stainless steel kettle and heated to about 75° C. The materials were mixed together until a clear solution was obtained.

The aqueous component, deionized water, of each vesicle preparation was weighed into a separate stainless steel kettle. Each solution was heated to about 65° C.

Using a Novamix™ lipid vesicle machine (described in U.S. Pat. No. 4,895,452), the lipid and aqueous components were mixed together for each formulation. Each resulting mixture was stirred continuously and allowed to cool to room temperature, about 25° C. An antibacterial agent was then added to the cooled solution, and the resulting solution was mixed until homogeneous before being stored.

The vesicles of each formulation were transferred directly from storage to a spraying apparatus, without being further diluted. Each of the formulations was sprayed onto a black and white surface and analyzed. All of the formulations were found to be satisfactory and commercially viable. Microscopic analysis revealed small, regular, spherical vesicles for each of the sample formulations, A1, B1, and C1, which formed a smooth, white, fluid lotion in an almost homogeneous population.

TABLE 1

| | Ingredients | A1 % (g) | B1 % (g) | C1 % (g) |
|---|---|---|---|---|
| LIPID PHASE | Polyethyleneglycol-4-olivate (Olivem 700) | 2.3 (1.15) | 4.5 (2.25) | 6.5 (3.25) |
| | Polyoxyethylene (20) sorbitan monooleate (Polysorbate 80 Kosher) | 1.0 (0.50) | 1.0 (0.50) | 1.0 (0.50) |
| | Cholesterol USP (Maypro) | 0.3 (0.15) | 0.5 (0.25) | 0.7 (0.35) |
| | Mixture of caprylic and capric triglyceride (Captex 300) | 5.0 (2.50) | 10.0 (5.00) | 15.0 (7.50) |
| AQUEOUS PHASE | DI Water | 90.4 (45.20) | 83.0 (41.50) | 75.8 (37.90) |
| | GERMABEN II (ISP Van Dyk)* | 1.0 (0.50) | 1.0 (0.50) | 1.0 (0.50) |
| pH | | 6.24 | 6.25 | 6.30 |

*propylene glycol, diazolidinyl urea, methylparaben, and propylparaben

In this example, formulation A1 was stable at temperatures of about 25° C., about 40° C., and about 50° C. for at least 24 hours. Formulation B1 was stable at temperatures of about 40° C. and about 50° C. for at least one week. Formulation C1 was stable at a temperature of about 40° C. for at least two weeks.

Example 2: Preparation of Lipid Vesicle Compositions Using Polyethvyeneglycol-4-Olivate and Mineral Oil The lipid vesicles of this Example were made using polyetheneglycol-4-olivate. Table 2 lists the materials and proportions used in preparing three different formulations of 50 g preparations of the lipid vesicles of this invention. The vesicles were formed under shear mixing conditions, as outlined above, using the procedure from Example 1. Microscopic analysis revealed small, regular, spherical vesicles for each of the sample formulations, A2, B2, and C2. Formulation A2 formed a smooth, white, fluid lotion. Formulation B2 formed a smooth, white, thin lotion. Formulation C2 formed a smooth, white, thick lotion with slight to moderate aggregations of the spherical vesicles.

TABLE 2

|  | Ingredients | A2 % (g) | B2 % (g) | C2 % (g) |
|---|---|---|---|---|
| LIPID PHASE | Polyethyleneglycol-4-olivate (Olivem 700) | 2.3 (1.15) | 4.5 (2.25) | 7.0 (3.50) |
|  | Cholesterol USP (Maypro) | 0.3 (0.15) | 0.5 (0.25) | 0.7 (0.35) |
|  | Mineral oil | 5.0 (2.50) | 5.0 (2.50) | 5.0 (2.50) |
| AQUEOUS PHASE | DI Water | 91.4 (45.70) | 89.0 (44.50) | 86.3 (43.15) |
|  | GERMABEN II (ISP Van Dyk)* | 1.0 (0.50) | 1.0 (0.50) | 1.0 (0.50) |
| pH |  | 6.23 | 6.19 | 6.06 |

*propylene glycol, diazolidinyl urea, methylparaben, and propylparaben

In this example, formulations A2, B2, and C2 were physically stable at temperatures of about 25° C.

Example 3: Preparation of Lipid Vesicle Compositions Using Sorbitan Olivate

The lipid vesicles of this Example were made using sorbitan olivate. Table 3 lists the materials and proportions used in preparing three different formulations of 50 g preparations of the lipid vesicles of this invention. The vesicles were formed under shear mixing conditions, as outlined above, using the procedure from Example 1. Microscopic analysis revealed large, irregular vesicles for each of the sample formulations, A3, B3, and C3. Formulations A3 and B3 each formed a white, fluid lotion. Formulation C3 formed a white, thin lotion with large aggregates.

TABLE 3

|  | Ingredients | A3 % (g) | B3 % (g) | C3 % (g) |
|---|---|---|---|---|
| LIPID PHASE | Sorbitan olivate (Olivem 900) | 2.3 (1.15) | 4.5 (2.25) | 7.0 (3.50) |
|  | Cholesterol USP (Maypro) | 0.3 (0.15) | 0.5 (0.25) | 0.7 (0.35) |
|  | Mineral oil | 5.0 (2.50) | 5.0 (2.50) | 5.0 (2.50) |
| AQUEOUS PHASE | DI Water | 91.4 (45.70) | 89.0 (44.50) | 86.3 (43.15) |
|  | GERMABEN II (ISP Van Dyk)* | 1.0 (0.50) | 1.0 (0.50) | 1.0 (0.50) |
| pH |  | 6.08 | 6.28 | 6.48 |

*propylene glycol, diazolidinyl urea, methylparaben, and propylparaben

All formulations of this example were physically stable.

Example 4: Preparation of Lipid Vesicle Compositions Using Cetearyl Olivate and Sorbitan Olivate, and Mineral Oil The lipid vesicles of this Example were made using cetaryl olivate and sorbitan olivate. Table 4 lists the materials and proportions used in preparing three different formulations of 50 g preparations of the lipid vesicles of this invention. The vesicles were formed under shear mixing conditions, as outlined above, using the procedure from Example 1. Microscopic analysis revealed formulations A4 and B4 each formed a smooth, white, thin lotion with vesicles of non-uniform size in a heterogeneous population. Formulation C4 formed a white, thin lotion with small spherical vesicles and some non-spherical aggregates in a heterogeneous population.

TABLE 4

|  | Ingredients | A4 % (g) | B4 % (g) | C4 % (g) |
|---|---|---|---|---|
| LIPID PHASE | Cetaryl and sorbitan olivate (Olivem 1000) | 2.3 (1.15) | 4.5 (2.25) | 7.0 (3.50) |
|  | Cholesterol USP (Maypro) | 0.3 (0.15) | 0.5 (0.25) | 0.7 (0.35) |
|  | Mineral oil | 5.0 (2.50) | 5.0 (2.50) | 5.0 (2.50) |
| AQUEOUS PHASE | DI Water | 91.4 (45.70) | 89.0 (44.50) | 86.3 (43.15) |
|  | GERMABEN II (ISP Van Dyk)* | 1.0 (0.50) | 1.0 (0.50) | 1.0 (0.50) |
| pH |  | 6.25 | 6.26 | 6.18 |

*propylene glycol, diazolidinyl urea, methylparaben, and propylparaben

In this example, formulations B4 and C4 were stable at temperatures of about 25° C., about 40° C., and about 50° C. for at least four weeks. Formulation A4 had little to no separation at temperatures of about 25° C. and about 40° C. for at least four weeks.

Example 5: Preparation of Lipid Vesicle Compositions Using Cetearyl Olivate and Sorbitan Olivate, Nonionic Detergent, and Triglyceride The lipid vesicles of this Example were made using cetaryl olivate and sorbitan olivate. Table 5 lists the materials and proportions used in preparing three different formulations of 50 g preparations of the lipid vesicles of this invention. The vesicles were formed under shear mixing conditions, as outlined above, using the procedure from Example 1. Microscopic analysis revealed that formulations A5, B5, and C5 each formed a smooth, white, thin lotion with small spherical vesicles in a heterogeneous population.

TABLE 5

|  | Ingredients | A5 % (g) | B5 % (g) | C5 % (g) |
|---|---|---|---|---|
| LIPID PHASE | Cetaryl and sorbitan olivate (Olivem 1000) | 2.3 (1.15) | 4.5 (2.25) | 6.0 (3.00) |
|  | Polyoxyethylene (20) sorbitan monooleate (Polysorbate 80 Kosher) | 1.0 (0.50) | 1.0 (0.50) | 1.0 (0.50) |
|  | Cholesterol USP (Maypro) | 0.3 (0.15) | 0.5 (0.25) | 0.7 (0.35) |
|  | Mixture of caprylic and capric triglyceride (Captex 300) | 5.0 (2.50) | 10.0 (5.00) | 15.0 (7.50) |
| AQUEOUS PHASE | DI Water | 90.4 (45.20) | 83.0 (41.50) | 76.3 (38.15) |
|  | GERMABEN II (ISP Van Dyk)* | 1.0 (0.50) | 1.0 (0.50) | 1.0 (0.50) |
| pH |  | 6.69 | 6.55 | 6.79 |

*propylene glycol, diazolidinyl urea, methylparaben, and propylparaben

In this example, formulations B5 and C5 were stable at temperatures of about 25° C. and about 40° C. for at least four weeks. Formulation A5 had some separation.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

The invention claimed is:

1. A composition comprising paucilamellar lipid vesicles, wherein the lipid vesicles comprise:
   (a) a lipid phase comprising
      (i) about 2.3% to about 7.0% by weight of polyethylene glycol 4-olivate;
      (ii) about 0.3% to about 0.7% by weight of a sterol;
      (iii) about 5% to about 15% by weight of one or more oils; and
   (b) an aqueous phase comprising about 75% to about 95% by weight of water,
wherein the lipid vesicles in the composition are homogeneous and stable at 25° C. for at least one week.

2. The composition of claim 1, wherein said aqueous phase further comprises an antimicrobial agent.

3. The composition of claim 1, wherein said sterol is selected from the group consisting of cholesterol, cholesterol derivatives, cholesterol salts, cholesterol esters, ethoxylated cholesterol, hydrocortisone, phytosterol, avocado unsaponifiables and mixtures thereof.

4. The composition of claim 1, wherein said one or more oils is a triglyceride selected from the group consisting of caprylic triglyceride, capric triglyceride, and mixtures thereof.

5. The composition of claim 1, wherein said one or more oils is a hydrocarbon.

6. The composition of claim 1, wherein said hydrocarbon is mineral oil.

7. The composition of claim 1, wherein said lipid phase further comprises a nonionic detergent.

8. The composition of claim 7, wherein said nonionic detergent is selected from the group consisting of polyoxyethylene (20) sorbitan monooleate, polyoxyethylene (20) sorbitan trioleate, polyoxyethylene (20) sorbitan monopalmitate, polyoxyethylene (20) sorbitan monostearate, and mixtures thereof.

9. The composition of claim 2, wherein said antimicrobial agent is a composition comprising propylene glycol, diazolidinyl urea, methylparaben, and propylparaben.

10. The composition of claim 1, wherein the pH is between about 2 to about 8.

11. The composition of claim 1, wherein said paucilamellar lipid vesicles have 2-10 lipid bilayers surrounding an amorphous central cavity.

12. The composition of claim 7, wherein the sterol is polyoxyethylene (20) sorbitan monooleate, the sterol is cholesterol, and the oil comprises caprilic triglyceride and capric triglyceride.

13. The composition of claim 1, wherein the sterol is cholesterol and the oil is mineral oil.

14. The composition of claim 1, wherein the lipid vesicles comprise:
    (a) a lipid phase comprising,
        (i) about 2.3% by weight of polyethylene glycol 4-olivate;
        (ii) about 1.0% by weight of polyoxyethylene (20) sorbitan monooleate;
        (iii) about 0.3% by weight of cholesterol; and
        (iii) about 5.0% by weight of a mixture of caprilic triglyceride and capric triglyceride; and
    (b) an aqueous phase comprising,
        (i) about 90.4% by weight of water; and
        (ii) about 1.0% of an antimicrobial agent comprising propylene glycol, diazolidinyl urea, methylparaben and propylparaben,
    wherein the pH of the composition is about 6.2-6.3.

15. The composition of claim 1, wherein the lipid vesicles comprise:
    (a) a lipid phase comprising,
        (i) about 4.5% by weight of polyethylene glycol 4-olivate;
        (ii) about 1.0% by weight of polyoxyethylene (20) sorbitan monooleate;
        (iii) about 0.5% by weight of cholesterol; and
        (iv) about 10.0% by weight of a mixture of caprilic triglyceride and capirc triglyceride; and
    (b) an aqueous phase comprising,
        (i) about 83% by weight of water; and
        (ii) about 1% of an antimicrobial agent comprising propylene glycol, diazolidinyl urea, methylparaben and propylparaben,
    wherein the pH of the composition is about 6.2-6.3.

16. The composition of claim 1, wherein the lipid vesicles comprise:
    (a) a lipid phase comprising,
        (i) about 6.5% by weight of polyethylene glycol 4-olivate;
        (ii) about 1.0% by weight of polyoxyethylene (20) sorbitan monooleate;
        (iii) about 0.7% by weight of cholesterol; and
        (iv) about 15.0% by weight of a mixture of caprilic triglyceride and capirc triglyceride; and
    (b) an aqueous phase comprising,
        (i) about 75.8% by weight of water; and
        (ii) about 1.0% of an antimicrobial agent comprising propylene glycol, diazolidinyl urea, methylparaben and propylparaben,
    wherein the pH of the composition is about 6.2-6.3.

17. The composition of claim 1, wherein the lipid vesicles comprise:
    (a) a lipid phase comprising,
        (i) about 2.3% by weight of polyethylene glycol 4-olivate;
        (ii) about 0.3% by weight of cholesterol; and
        (iii) about 5.0% by weight of mineral oil; and
    (b) an aqueous phase comprising,
        (i) about 91.4% by weight of water; and
        (ii) about 1.0% of an antimicrobial agent comprising propylene glycol, diazolidinyl urea, methylparaben and propylparaben,
    wherein the pH of the composition is about 6.2-6.3.

18. The composition of claim 1, wherein the lipid vesicles comprise:
    (a) a lipid phase comprising,
        (i) about 4.5% by weight of polyethylene glycol 4-olivate;
        (ii) about 0.5% by weight of cholesterol; and
        (iii) about 5.0% by weight of mineral oil; and
    (b) an aqueous phase comprising,
        (i) about 89.0% by weight of water; and
        (ii) about 1.0% of an antimicrobial agent comprising propylene glycol, diazolidinyl urea, methylparaben and propylparaben,
    wherein the pH of the composition is about 6.2.

* * * * *